United States Patent
Vernickel et al.

(10) Patent No.: US 11,982,722 B2
(45) Date of Patent: May 14, 2024

(54) AUTOMATED DETECTION OF RECEIVE COIL LOCATION

(71) Applicant: KONINKLIJKE PHILIPS N.V., Eindhoven (NL)

(72) Inventors: Peter Vernickel, Hamburg (DE); Christoph Gunther Leussler, Hamburg (DE); Oliver Lips, Hamburg (DE); Ingo Schmale, Hamburg (DE); Christian Findeklee, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 408 days.

(21) Appl. No.: 17/421,759

(22) PCT Filed: Jan. 10, 2020

(86) PCT No.: PCT/EP2020/050471
§ 371 (c)(1),
(2) Date: Jul. 9, 2021

(87) PCT Pub. No.: WO2020/144300
PCT Pub. Date: Jul. 16, 2020

(65) Prior Publication Data
US 2022/0091202 A1      Mar. 24, 2022

(30) Foreign Application Priority Data
Jan. 11, 2019 (EP) .................................. 19151321

(51) Int. Cl.
*A61B 5/05* (2021.01)
*A61B 5/055* (2006.01)
(Continued)

(52) U.S. Cl.
CPC ............ *G01R 33/283* (2013.01); *A61B 5/055* (2013.01); *G01R 33/341* (2013.01);
(Continued)

(58) Field of Classification Search
CPC .. G01R 33/283; G01R 33/341; G01R 33/543; G06T 7/70; G06T 7/80
See application file for complete search history.

(56) References Cited

U.S. PATENT DOCUMENTS

| 4,982,081 A * | 1/1991 | Schmidt .................. H04N 9/28 |
| | | 250/208.2 |
| 10,753,992 B2 | 8/2020 | Ortiz et al. |

(Continued)

FOREIGN PATENT DOCUMENTS

| CN | 102551736 A | 7/2012 |
| CN | 103654778 A | 3/2014 |

(Continued)

OTHER PUBLICATIONS

International Search Report and Written Opinion From PCT/EP2020/050471 dated Jul. 16, 2020.

*Primary Examiner* — Joel F Brutus

(57) ABSTRACT

The invention provides for a magnetic resonance imaging system (100, 300). The magnetic resonance imaging system comprises: a subject support (120) configured for moving a subject between a loading position (121) and an imaging position (200); a receive magnetic resonance imaging coil (114) configured for being placed on the subject; and a light detection system (115) comprising at least one ambient light sensor for measuring light data (144). The light detection system is any one of the following: mounted to the main magnet such that the light data is measured from the imaging zone and mounted to the receive magnetic resonance imaging coil. The execution of the machine executable (140) instructions by a processor (130) cause the processor to: move (500) the subject support from the loading position to the imaging position; acquire (502) the light data using the at least one ambient light sensor when the subject support is in the imaging position; determine (504) if the receive magnetic resonance imaging coil is positioned for acquiring magnetic resonance imaging data using the light data; and provide (506) a signal (146) if the receive magnetic resonance imaging coil is positioned for acquiring the magnetic resonance imaging data.

20 Claims, 10 Drawing Sheets

(51) Int. Cl.
*G01R 33/28* (2006.01)
*G01R 33/341* (2006.01)
*G01R 33/54* (2006.01)
*G06T 7/70* (2017.01)
*G06T 7/80* (2017.01)

(52) U.S. Cl.
CPC .............. *G01R 33/543* (2013.01); *G06T 7/70* (2017.01); *G06T 7/80* (2017.01)

(56) References Cited

U.S. PATENT DOCUMENTS

| | | | |
|---|---|---|---|
| 2005/0283068 A1* | 12/2005 | Zuccolotto | G01R 33/283 600/410 |
| 2009/0262551 A1* | 10/2009 | Trowell | G01R 33/28 362/253 |
| 2010/0156421 A1 | 6/2010 | Sukkau | |
| 2010/0182005 A1* | 7/2010 | Biber | G01R 33/341 324/318 |
| 2012/0112748 A1* | 5/2012 | Hetherington | G01R 33/365 324/318 |
| 2013/0060129 A1 | 3/2013 | Lee et al. | |
| 2013/0085377 A1* | 4/2013 | Barbot | A61B 5/062 600/417 |
| 2013/0119981 A1 | 5/2013 | Choi et al. | |
| 2015/0260821 A1 | 9/2015 | Biber et al. | |
| 2016/0338614 A1 | 11/2016 | Gall et al. | |
| 2017/0176552 A1 | 6/2017 | Reykowski | |

FOREIGN PATENT DOCUMENTS

| | | |
|---|---|---|
| EP | 2568307 A1 | 3/2013 |
| EP | 3349030 A1 | 7/2018 |
| JP | 2005124855 A | 5/2005 |
| WO | 2017077435 A1 | 5/2017 |

* cited by examiner

AUTOMATED DETECTION OF RECEIVE COIL LOCATION

CROSS REFERENCE TO RELATED APPLICATIONS

This application is a U.S. national phase application of International Application No. PCT/EP2020/050471 filed on Jan. 10, 2020, which claims the benefit of EP Application Serial No. 19151321.7 filed on Jan. 11, 2019 and is incorporated herein by reference.

FIELD OF THE INVENTION

The invention relates to magnetic resonance imaging.

BACKGROUND OF THE INVENTION

A large static magnetic field is used by Magnetic Resonance Imaging (Mill) scanners to align the nuclear spins of atoms as part of the procedure for producing images within the body of a subject. This large static magnetic field is referred to as the B0 field or the main magnetic field. Various quantities or properties of the subject can be measured spatially using MRI. Various imaging protocols can be implemented by using pulse sequences to control the acquisition of magnetic resonance data.

Chinese patent publication CN 103654778 B discloses a positioning system and a magnetic resonance imaging control method, the magnetic resonance system comprises a resonance host, and a movable deck local coil, the main deck is moved into within the magnetic resonance volume, the magnetic resonance host receiving means provided with an optical signal, a light signal emitting apparatus is mounted on the deck or local coil. This patent also discloses an imaging control method that uses an optical signal receiving apparatus and an optical signal transmitting means in a stepping mode to quickly locate mode to automatically position the patient MM regional center, thereby simplifying positioning, imaging operation, and increase the positioning accuracy, saving the cost of inspection, better meet the practical imaging needs.

The US patent application US2013/0119981 discloses a magnetic resonance imaging apparatus with a wireless RF coil and a sensor unit. The sensor unit may be an optical sensor that detects optical signals from a laser transmission unit in the gantry's interior of the MM system.

SUMMARY OF THE INVENTION

The invention provides for a magnetic resonance imaging system, a method, and a computer program product in the independent claims.

Configuring a magnetic resonance imaging system for use can be complicated. Failures during imaging protocols or calibration protocols may be due to hardware failures and/or an incorrect configuration of the subject for imaging. Often time a receive magnetic resonance imaging coil such as a surface coil may be used with a subject. If the receive magnetic resonance imaging coils is placed incorrectly the magnetic resonance imaging protocol may fail. Embodiments may provide for a means of detecting if the receive magnetic resonance imaging coil is placed properly on the subject by detecting a change in the ambient light. If an ambient light sensor is placed on the receive magnetic resonance imaging coil directly then a change in the detected light between a loading and an imaging position of the subject can be detected. Likewise placing the ambient light sensor in the bore of a magnetic resonance imaging coil, such as in or near the imaging zone, may allow the detection of proper location of the receive magnetic resonance imaging coil also. The present invention concerns a magnetic resonance imaging system with a light detection system to determine the position of a magnetic resonance imaging coil (local radiofrequency (RF) antenna). According to the invention, the light detection system operates on the basis of ambient illumination. The ambient illumination is spatially encoded in that at least the ambient illumination has a physical aspect that is different between the loading and imaging positions, respectively of the subject support.

The present invention achieves that the position of the magnetic resonance imaging coil can be detected to be in the imaging position or in the loading position without the need of separate optical hardware in the examination zone of the magnetic resonance imaging system.

In one aspect the invention provides for a magnetic resonance imaging system that is configured for acquiring magnetic resonance imaging data from an imaging zone. The magnetic resonance imaging system comprises a main magnet configured for generating a B0 or main magnetic field within the imaging zone. The magnetic resonance imaging system further comprises a subject support configured for moving a subject between a loading position and an imaging position. When the subject is in the loading position the subject is not within the imaging zone. When the subject is in the imaging position the subject is at least partially within the imaging zone. The magnetic resonance imaging system further comprises a receive magnetic resonance imaging coil configured for being placed on the subject. Receive magnetic resonance imaging coils of this type are typically referred to as surface coils. The receive magnetic resonance imaging coil in some examples may also be flexible.

The magnetic resonance imaging system further comprises a light detection system comprising at least one ambient light sensor for measuring light data. An ambient light sensor as used herein is a sensor which is configured for detecting light and collecting it from an area surrounding the sensor. The light detection system is any one of the following: a) mounted to the main magnet such that the light data is measured from the imaging zone and b) mounted to the receive magnetic resonance imaging coil. Being mounted to the main magnet may include being mounted to any of the components attached to the main magnet or which are used to form the main magnet. For example, being mounted to the main magnet may include the housing of a body coil or other components.

The magnetic resonance imaging system further comprises a memory that stores machine-executable instructions. The magnetic resonance imaging system further comprises a processor for controlling the magnetic resonance imaging system. Execution of the machine-executable instructions causes the processor to move the subject support from the loading position to the imaging position.

Execution of the machine-executable instructions further causes the processor to acquire the light data using the at least one ambient light sensor when the subject support is in the imaging position. Execution of the machine-executable instructions further causes the processor to determine if the receive magnetic resonance imaging coil is positioned for acquiring the magnetic resonance imaging data using the light data. Execution of the machine-executable instructions further causes the processor to provide a signal if the receive magnetic resonance imaging coil is positioned for acquiring the magnetic resonance imaging data. The signal may for instance indicate if the coil is in the proper position or not in the proper position. The signal may take different forms in different examples. In one example it may be a warning or other indicator to indicate if the magnetic resonance imaging coil is not positioned in a position where it can acquire the magnetic resonance imaging data. The signal may also take the form of a data which is provided to other computing or software components and may be used for further control of the magnetic resonance imaging system.

This embodiment may be beneficial because the signal may serve as an independent check on the operation of the magnetic resonance imaging system. The measurement of the light data is performed after the subject support was already loaded into the imaging position. A knowledge if the coil is then in the proper position may be used to compare if various other components of the magnetic resonance imaging system are functioning properly. For example, if the subject support is functioning properly and is actually moving the subject into the loading position. The signal may also be used to check the operation of the radio-frequency system during a calibration of the radio-frequency system and associated radio-frequency or imaging coils attached to it. For example, the receive magnetic resonance imaging coil may be calibrated or configured prior to acquiring magnetic resonance data. The signal can be used to determine if a failure of this calibration is due to a failure of configuration of the subject and the receive magnetic resonance imaging coil or it may be possibly a failure due to the radio-frequency system.

In another embodiment, the main magnet is a cylindrical magnet with a bore. The light detection system is mounted to the bore. The light detection system can be arranged or attached such that the light data is measured from the imaging zone.

In another embodiment the magnetic resonance imaging system further comprises a multi-channel radio-frequency system configured for acquiring the magnetic resonance imaging data. The radio-frequency system comprises a body coil and the receive magnetic resonance imaging coil. The receive magnetic resonance imaging coil comprises multiple receive elements. The memory further contains calibration commands configured for controlling the magnetic resonance imaging system to perform a calibration of the multiple receive elements of the receive magnetic resonance imaging coil using the body coil.

Execution of the machine-executable instructions further causes the processor to calibrate the multiple channels of the receive magnetic resonance imaging coil by executing the calibration commands. Execution of the machine-executable instructions further causes the processor to provide a hardware failure signal if the calibration fails with the signal indicating that the receive magnetic resonance imaging coil is properly positioned. This embodiment may be advantageous because it may provide for a means of independently controlling if the radio-frequency system of the magnetic resonance imaging system is functioning properly.

In another embodiment the light detection system is mounted to the receive magnetic resonance imaging coil. This embodiment may be advantageous because it may be possible to implement it without any specialized sources of light provided in the room and/or the magnet. The properties of the light outside of the magnetic resonance imaging system and also within the imaging zone of the magnet may be different. For example, light may have different frequencies and/or brightness which can be detected by the at least one ambient light sensor. Relatively sophisticated or subtle changes in the light can be detected using the at least one ambient light sensor. Various means may be useful for determining this. For example, various measurements may be made with the coil outside of the magnet and then with the magnetic resonance imaging coil placed in the proper position. An analytic model with thresholds could be used to make this determination. In other examples machine learning may be useful for doing this. The machine learning may be useful for recognizing various patterns of light for a particular magnetic resonance imaging system.

In another embodiment the magnetic resonance imaging system comprises an examination room for housing the main magnet. The examination room comprises a room illumination system. The main magnet comprises a magnet illumination system for illuminating the imaging zone and also possibly the bore of the magnetic resonance imaging magnet. The room illumination system is configured for producing a first type of light. The magnet illumination system is configured for producing a second type of light. Execution of the machine-executable instructions causes the processor to determine if the receive magnetic resonance imaging coil is positioned for acquiring the magnetic resonance imaging data by differentiating between the first type of light and the second type of light. As was mentioned above this may be accomplished in a variety of different ways depending upon the difference between the first type of light and the second type of light. This may be done using analytical models or thresholding. In other examples a neural net may be useful for differentiating between the first type of light and the second type of light.

In another embodiment the first type of light differs from the second type of light by a color difference.

In another embodiment the first type of light differs from the second type of light by an intensity difference.

In another embodiment the first type of light differs from the second type of light by an oscillation frequency of the light.

In another embodiment the first type of light differs from the second type of light by an intensity of a color component.

In another embodiment the first type of light differs from the second type of light by a modulation of the first type of light and/or the second type of light.

In another embodiment the magnet illumination system is configured for producing light with a spatially dependent frequency and/or spatially dependent color encoding and/or spatially dependent modulation. This embodiment may be beneficial because using the spatial dependence in the illumination system the position of the receive magnetic resonance imaging coil may be better determined or more accurately determined.

In another embodiment execution of the machine-executable instructions further causes the processor to determine a spatial position and/or orientation of the receive magnetic resonance imaging coil using the spatially dependent frequency, the spatially dependent color encoding, or spatially dependent modulation produced by the magnet illumination system.

In another embodiment the light detection system comprises multiple ambient light sensors configured for measuring ambient light distributed across a surface of the receive magnetic resonance imaging coil. This embodiment may be beneficial because the use of multiple sensors may enable more accurate determination of the position and/or orientation of the receive magnetic resonance imaging coil.

In another embodiment the receive magnetic resonance imaging coil comprises a preamplifier. The at least one ambient light sensor is attached to the preamplifier. The receive magnetic resonance imaging coil comprises an optical fiber configured for each of the at least one ambient light sensor for channeling light from the surface of the receive magnetic resonance imaging coil to the at least one ambient light sensor. This embodiment may be beneficial because all of the active electronics are moved to where the location of the preamplifier is. Putting the ambient light sensor within the or adjacent to the coil elements of the receive magnetic resonance imaging coil may make it more difficult or degrade the acquisition of the magnetic resonance imaging data. Using the fiber optics may therefore increase the quality of magnetic resonance imaging data measured with the antenna.

In another embodiment the light detection system is mounted to the main magnet such that the light data is measured from the imaging zone. The receive magnetic resonance imaging coil comprises at least one light generating element. This embodiment may be beneficial because the ambient light sensor within the main magnet may be used to detect when the receive magnetic resonance imaging coil is then placed within the vicinity of the detector.

In various embodiments or examples the receive magnetic resonance imaging coil may produce light which has a spatially dependent frequency, a color encoding, and/or a modulation which can be detected by the light detection system of the main magnet. This may enable identification and/or more precise locating of the receive magnetic resonance imaging coil.

In another embodiment execution of the machine-executable instructions causes the processor to determine if the receive magnetic resonance imaging coil is positioned for acquiring the magnetic resonance imaging data by inputting the light data into a decision module programmed to compare the light data to the predetermined criteria. The decision module may be beneficial because the conditions which trigger the receive magnetic resonance imaging coil being in the proper position can be analytically determined and programmed.

In another embodiment execution of the machine-executable instructions further cause the processor to determine if the receive magnetic resonance imaging coil is positioned for acquiring the magnetic resonance imaging data by inputting the light data into a training machine learning module. For example, a neural network may be trained using deep learning to recognize when the magnetic resonance imaging coil is in the proper position. This may be beneficial because it may be straight forward to configure or train the trained machine learning module for a specific magnetic resonance imaging system.

In another embodiment the magnetic resonance imaging system further comprises an optical data transmission system. For example, both the main magnet and the receive magnetic resonance imaging coil could have both optical emitters and sensors which enables the exchange of data. The optical data transmission system is configured for forming a bi-directional data link between the receive magnetic resonance imaging coil and the processor. The optical data transmission system comprises the light detection system. This could be used for different purposes. In some instances, it may be useful for locating the position of the receive magnetic resonance imaging coil more precisely or it might also be used for positively identifying the particular receive magnetic resonance imaging coil or even its type of imaging coil.

In another aspect the invention provides for a computer program product comprising machine-executable instructions for execution by a processor controlling the magnetic resonance imaging system. The magnetic resonance imaging system is configured for acquiring magnetic resonance imaging data from an imaging zone. The magnetic resonance imaging system comprises a main magnet configured for generating a B0 magnetic field within the imaging zone. The magnetic resonance imaging system further comprises a subject support configured for moving the subject between a loading position and an imaging position. The magnetic resonance imaging system further comprises a receive magnetic resonance imaging coil configured for being placed on the subject. The magnetic resonance imaging system further comprises a light detection system comprising at least one ambient light sensor for measuring light data.

The light detection system is any one of the following: mounted to the main magnet such that the light data is measured from the imaging zone and mounted to the magnetic resonance imaging coil. Execution of the machine-executable instructions causes the processor to move the subject support from the loading position to the imaging position. Execution of the machine-executable instructions further causes the processor to acquire the light data using the at least one ambient light sensor when the subject support is in the imaging position. Execution of the machine-executable instructions further causes the processor to determine if the receive magnetic resonance imaging coil is positioned for acquiring the magnetic resonance imaging data using the light data. Execution of the machine-executable instructions further causes the processor to provide a signal if the receive magnetic resonance imaging coil is positioned for acquiring the magnetic resonance imaging data. The advantages of this have been previously discussed.

In another aspect the invention provides for a method of operating a magnetic resonance imaging system. The magnetic resonance imaging system is configured for acquiring magnetic resonance imaging data from an imaging zone. The magnetic resonance imaging system comprises a main magnet configured for generating a B0 magnetic field within the imaging zone. The magnetic resonance imaging system further comprises a subject support configured for moving a subject between a loading position and an imaging position. The magnetic resonance imaging system further comprises a receive magnetic resonance imaging coil configured for being placed on the subject. The magnetic resonance imaging system further comprises a light detection system comprising at least one ambient light sensor for measuring light data. The light detection system is any one of the following: mounted to the main magnet such that the light data is measured from the imaging zone and mounted to the magnetic resonance imaging coil. The method comprises moving the subject support from the loading position to the imaging position. The method further comprises acquiring the light data using the at least one ambient light sensor when the subject support is in the imaging position. The method further comprises determining if the receive magnetic resonance imaging coil is positioned for acquiring the magnetic resonance imaging data using the light data. The method further comprises providing a signal if the receive magnetic resonance imaging coil is positioned for acquiring the magnetic resonance imaging data. The advantages of this have been previously discussed.

In another aspect, the invention provides for a receive magnetic resonance imaging coil that comprises a preamplifier. At least one ambient light sensor is attached to the preamplifier. The receive magnetic resonance imaging coil comprises an optical fiber for each of the at least one ambient light sensor. Each optical fiber is configured for channeling light from the surface of the receive magnetic resonance imaging coil to one of the at least one ambient light sensor.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance Imaging (MRI) data is defined herein as being the recorded measurements of radio frequency signals emitted by atomic spins using the antenna of a Magnetic resonance imaging apparatus during a magnetic resonance imaging scan. A Magnetic Resonance image or MR image is defined herein as being the reconstructed two or three-dimensional visualization of anatomic data contained within the magnetic resonance imaging data. This visualization can, for example, be performed using a computer.

An ambient light sensor as used herein may encompass the commercially available ambient light sensors used in consumer electronic products such as smartphones, automotive displays, LCT TVs, or notebook computers. Ambient light sensors are a commonly available electronic component. More broadly an ambient sensor may encompass a photodetector or photodiode that receives light from a sold angle that is larger than a chosen solid angle. The solid chosen angle may be greater than any one of the following: 3/2 Pi, Pi, ¾ Pi, and ½ Pi.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
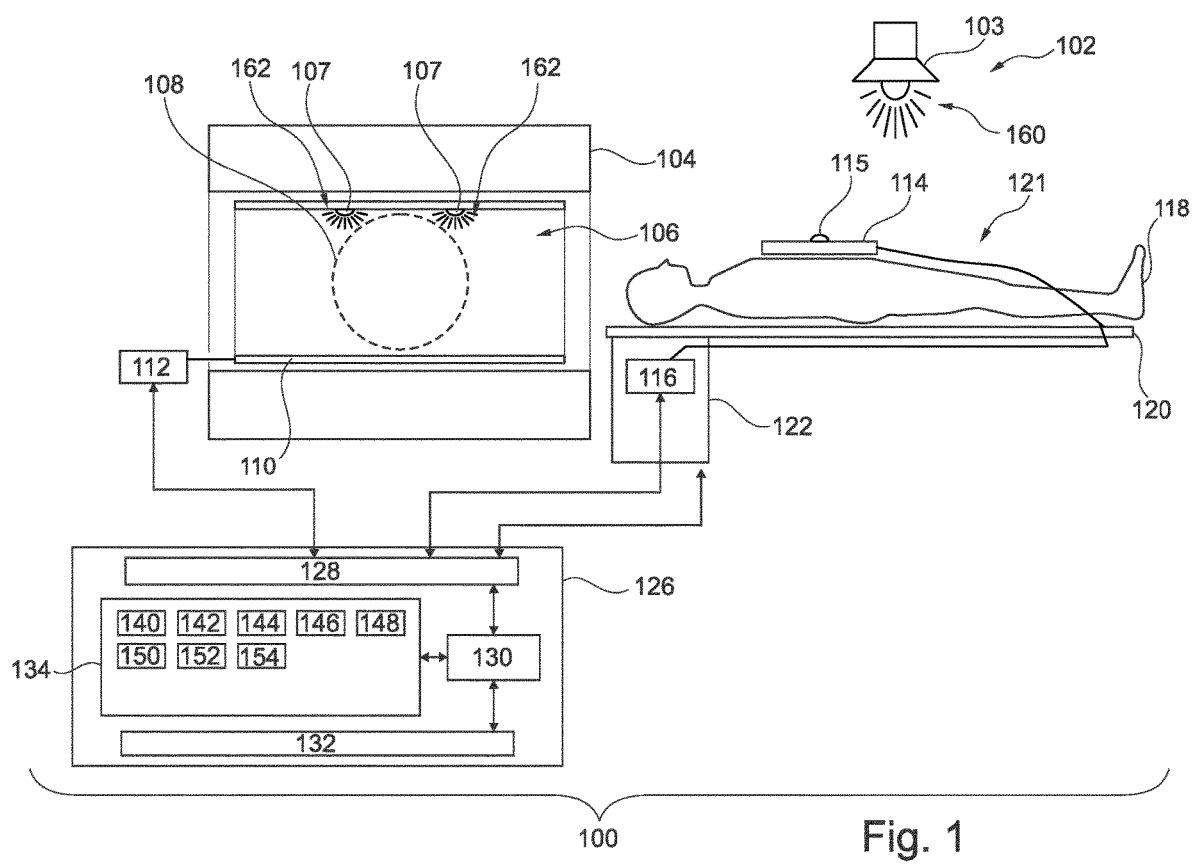
FIG. 1 illustrates an example of a magnetic resonance imaging system.

FIG. 1 illustrates an example of a magnetic resonance imaging system 100. The magnetic resonance imaging system 100 comprises an examination room 102 which has a room illumination system 103.

The magnetic resonance imaging system 100 comprises a magnet or main magnet 104. The magnet 104 is a superconducting cylindrical type magnet with a bore 106 through it. Within the bore of the magnet 106 there is a magnet illumination system 107. The room illumination system 103 produces a first type of light 160. The magnet illumination system 107 produces a second type of light 162.

The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

The subject 118 is shown as reposing on the subject support 120. There is a receive magnetic resonance imaging coil 114 which in this case is a surface coil. The receive magnetic resonance imaging coil 114 has an ambient light sensor 115 mounted on it. The subject support 120 is currently in a loading position 121. The ambient light sensor 115 is therefore exposed to the first type of light 160. The ambient light sensor 115 can measure or detect the presence of the first type of light 160 and make a determination that the subject 118 is in the loading position 121. There is an actuator 122 that is able to move the subject support 120 into the bore 106 of the magnet 104.

The receive magnetic resonance imaging coil 114 is for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency receiver or transceiver 116. The radio-frequency coil 114 and radio frequency transceiver 116 may be replaced by separate transmit and receive coils and a separate transmitter and receiver. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

The transceiver 116, the gradient controller 112, and the actuator 122 of the subject support 120 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 134 may be considered to be a non-transitory computer-readable medium.

The memory 134 is shown as containing machine-executable instructions 140. The machine-executable instructions 140 enable the processor 130 to send commands to control the various components of the magnetic resonance imaging system 100. The machine-executable instructions 140 also enable the processor 130 to perform various data analysis and data manipulation tasks. The memory 134 is further shown as containing pulse sequence commands 142 which enable the magnetic resonance imaging system 100 to acquire magnetic resonance imaging data from the subject 118 when the subject is within the imaging zone. The memory 134 is shown as containing light data 144 which is data which has been measured with the ambient light sensor 115. The memory 134 is also shown as containing initial light data 152. The initial light data 152 is light data which has been measured with the subject and the subject support 120 in the loading position 121. The initial light data 152 is therefore descriptive of the first type of light 160.

The memory 134 is further shown as containing a signal 146 which can be used to indicate if the receive magnetic resonance imaging coil 114 is in position to acquire magnetic resonance data from the imaging zone 108. The memory 134 is further shown as containing an optional decision module 148 which is able to use light data 144 which is acquired within the bore 106 of the magnet and optionally initial light data 152 to determine if the receive magnetic resonance imaging coil 114 is in the proper position for acquiring magnetic resonance data. The memory 134 is also shown as containing an optional training machine learning module 150 which could for example be a neural network that has been trained to recognize or differentiate the first type of light 160 from the second type of light 162.

Both the decision module 148 and/or the trained machine learning module 150 could be trained to also use the light data 144 to determine the position and/or orientation of the receive magnetic resonance imaging coil. The memory 134 is also shown as containing optional calibration commands 154 which enable the radio-frequency system 116 and the receive magnetic resonance imaging coil 114 to be calibrated once it is in position in the magnet. This for example may be used when the radio-frequency system 116 contains multiple receive channels for the receive magnetic resonance imaging coil 114.

Figure 2:
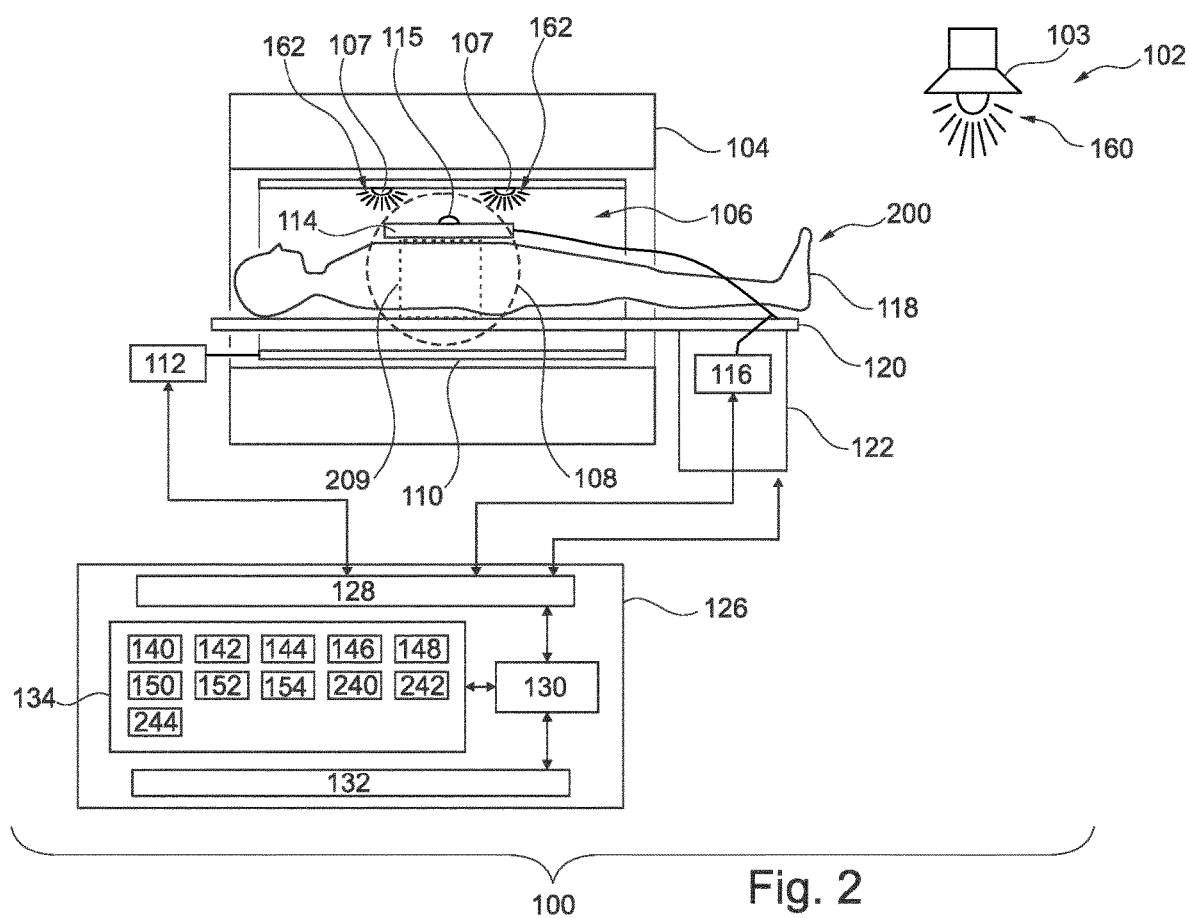
FIG. 2 shows a further view of the magnetic resonance imaging system of FIG. 1.

FIG. 2 shows a further view of the magnetic resonance imaging system 100 of FIG. 1. In this example the subject support 120 has been moved into an imaging position 200. The ambient light sensor 115 is now exposed to the second type of light 162 in the bore of the magnet 106. The light data 144 can then be used to make a determination that the receive magnetic resonance imaging coil 114 is in a proper position for acquiring magnetic resonance imaging data from a region of interest 209 within the imaging zone 108.

The first 160 and second 162 types of light could be differentiated in various ways such as the color, the oscillation frequency, a modulation frequency, a brightness, or the presence of various color components could be used for differentiation.

The computer memory 134 is further shown as containing a calibration result 240 resulting from executing the calibration commands 154. The calibration result 240 can be compared to the signal 146 to indicate if the magnetic resonance imaging system 100 is functioning properly and also if the execution of the pulse sequence commands 142 is allowed. The memory 134 is further shown as containing magnetic resonance imaging data 242 that has been acquired by controlling the magnetic resonance imaging system with the pulse sequence commands 142. The memory 134 is further shown as containing a magnetic resonance image 244 that has been reconstructed from the magnetic resonance imaging data 242.

Figure 3:
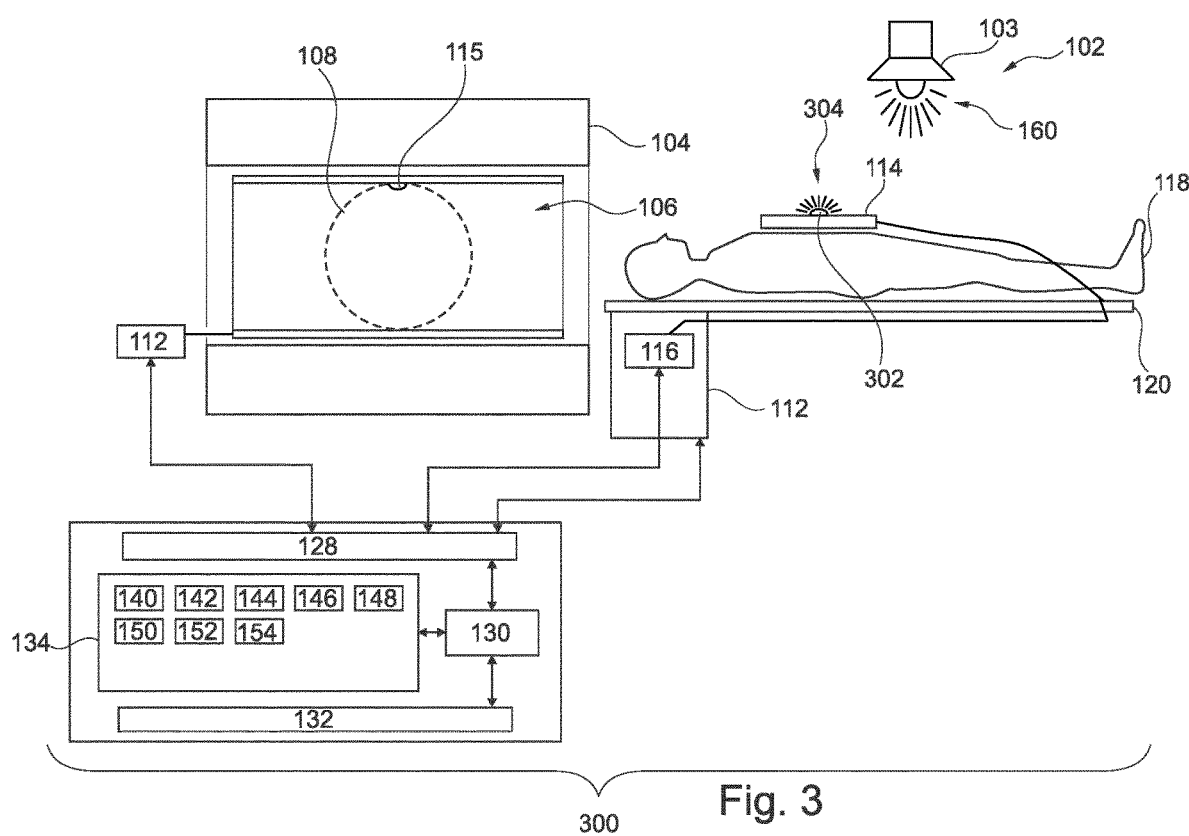
FIG. 3 illustrates a further example of a magnetic resonance imaging system.

FIG. 3 shows an alternative magnetic resonance imaging system 300. The magnetic resonance imaging system 300 depicted in FIG. 3 is similar to the magnetic resonance imaging system 100 illustrated in FIGS. 1 and 2 with the exception that the ambient light sensor is now mounted within the bore 106 of the magnet 104 and the receive magnetic resonance imaging coil 114 comprises a light generating element 302. The light generating element 302 generates light 304. The ambient light sensor 115 can detect the light 304 from the light generating element 302. The magnetic resonance imaging system is still shown as comprising the room illumination system 103 that generates light of a first type 160. This may or may not be present. The ambient light sensor 115 may not necessarily be sensitive to the first type of light 160 in all examples.

Figure 4:
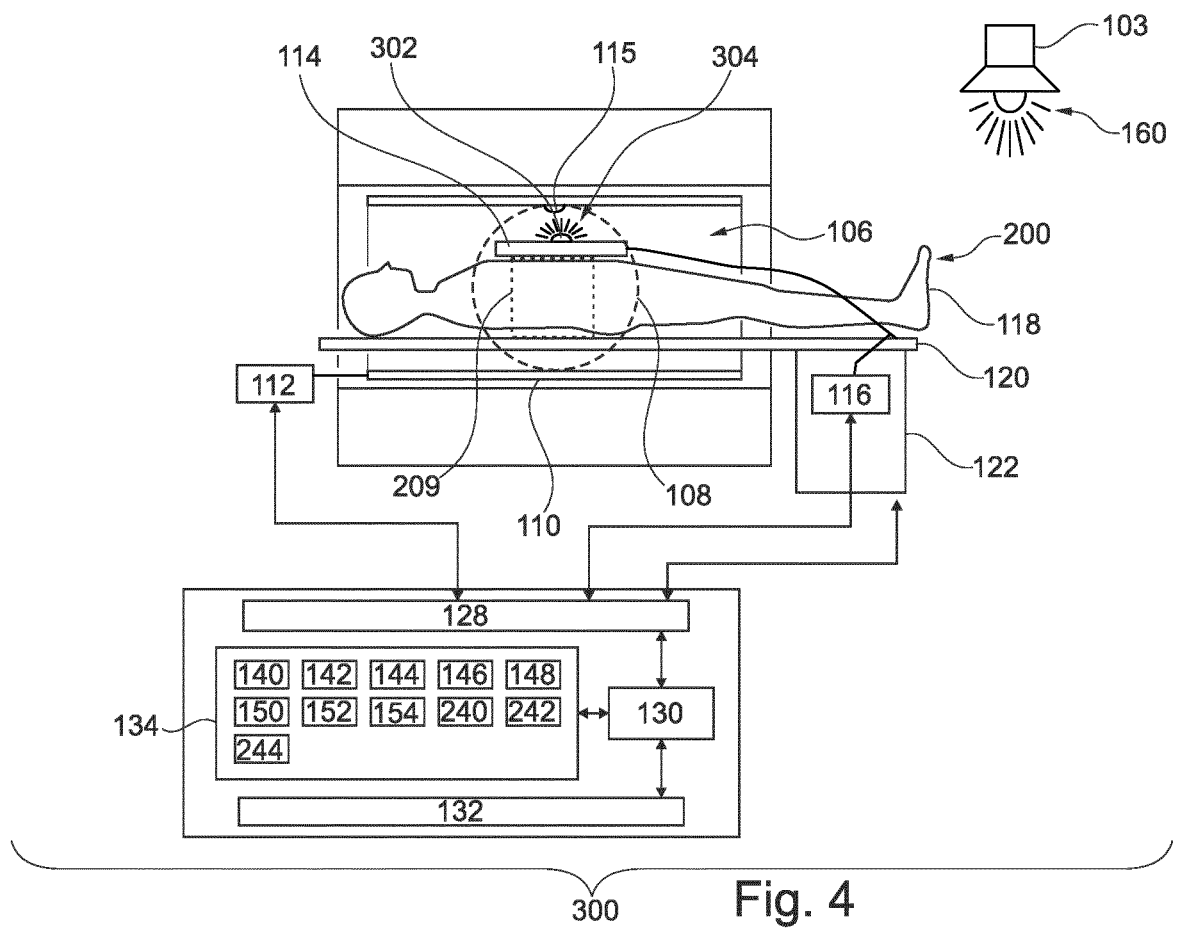
FIG. 4 shows a further view of the magnetic resonance imaging system of FIG. 1.

FIG. 4 shows a further view of the magnetic resonance imaging system 300 of FIG. 3. The view in FIG. 4 is analogous to the view illustrated in FIG. 3 for the other magnetic resonance imaging system 100. In this example in FIG. 4 we see that the subject support 120 has been moved into the imaging position 200. The light generating element 302 is now in proximity to the ambient light sensor 115. The ambient light sensor 115 is then able to detect that the receive magnetic resonance imaging coil 114 is in a proper position for acquiring the magnetic resonance imaging data 242.

Figure 5:
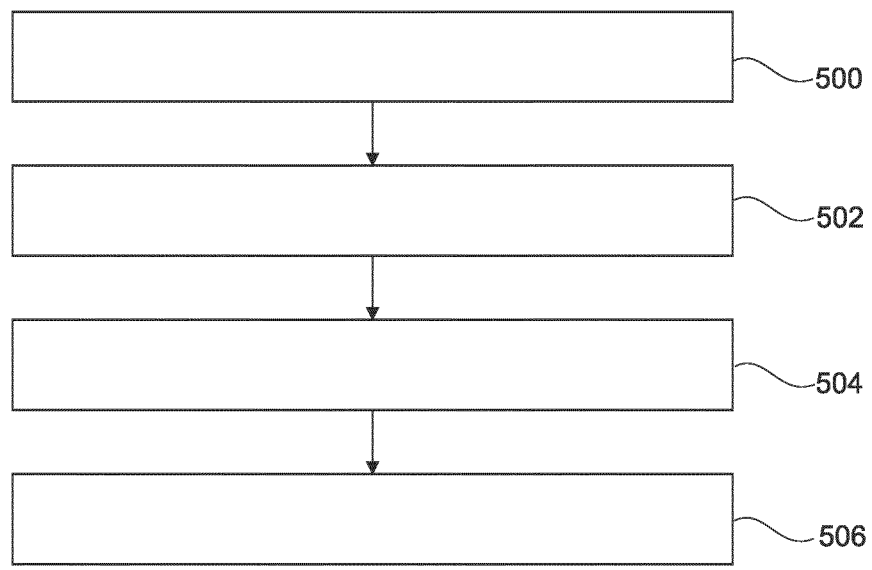
FIG. 5 illustrates a method of operating the magnetic resonance imaging system of FIG. 1 or 3.

FIG. 5 shows a flowchart which illustrates a method of operating either the magnetic resonance imaging system 100 of FIGS. 1 and 2 or the magnetic resonance imaging system 300 illustrated in FIGS. 3 and 4. First in step 500 the subject support 120 is moved from the loading position 121 to the imaging position 200. Next in step 502 the light data 144 is acquired using the ambient light sensor 115. This is done when the subject support 120 is in the imaging position 200. Next in step 504 it is determined if the receive magnetic resonance imaging coil 114 is positioned for acquiring the magnetic resonance imaging data 242 using the light data 144. This for example could be performed using either the decision module 148 or the trained machine learning module 150. Finally, in step 506, the signal 146 is provided if the receive magnetic resonance imaging coil 114 is positioned for acquiring the magnetic resonance imaging data 242.

In the examples illustrated in FIGS. 1-4 the ambient light sensor 115 is able to tell roughly if the receive magnetic resonance imaging coil 114 is positioned properly. It is however possible to provide a larger number of ambient light sensors 115 and/or magnet illumination systems 107 and/or light generating elements so that the position and orientation of the receive magnetic resonance imaging coil 114 can be determined.

Figure 6:
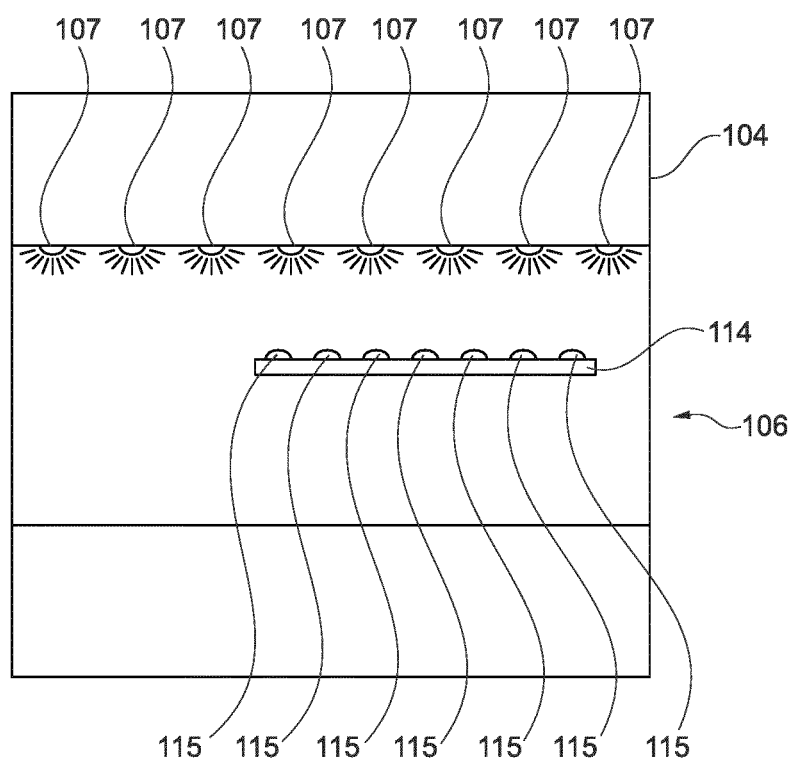
FIG. 6 illustrates a further example of a magnetic resonance imaging system.

FIG. 6 illustrates an example where the linear position along the axis of the magnet can be determined. In this example there are multiple ambient light sensors 115 on the receive magnetic resonance imaging coil 114. There are then a number of magnet lights for the magnet illumination system 107. The property of the light generated by the magnet illumination system 107 can vary linearly. For example, the color, the oscillation frequency, the modulation of the light, a color component or other characteristics can be varied so that the various ambient light sensors 115 can detect changes in the measured ambient light. As an alternative, a large number of light generating elements can be used to replace the ambient light sensors 115 and the ambient light sensors can be mounted instead on the bore 106 of the magnet 104.

Figure 7:
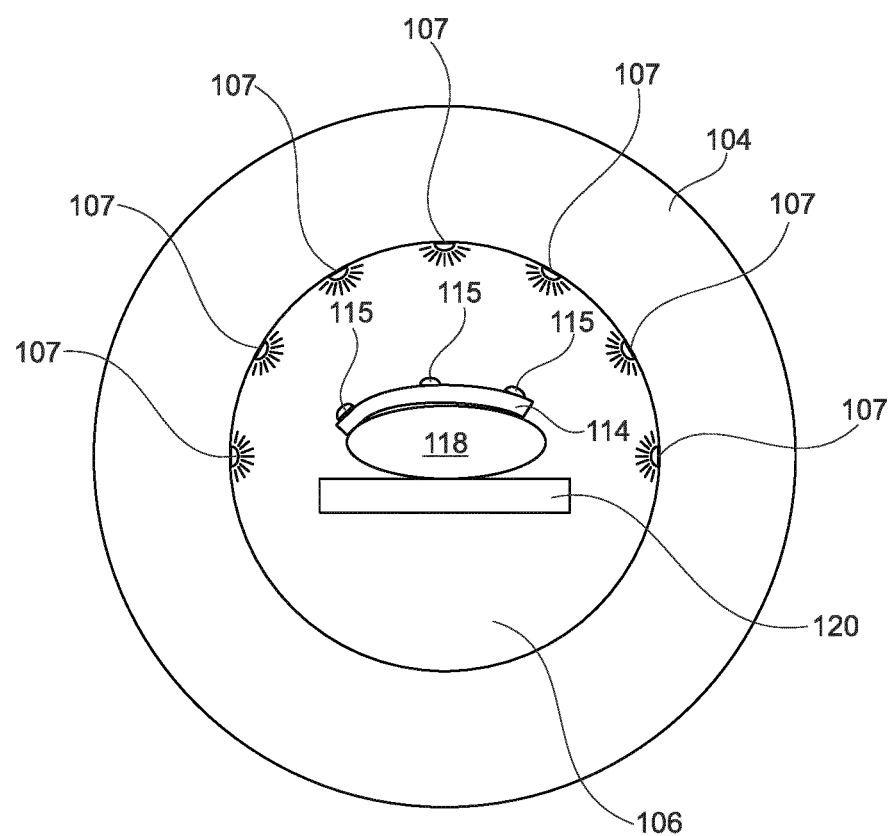
FIG. 7 illustrates a further example of a magnetic resonance imaging system.

FIG. 7 illustrates a further example of being able to determine the orientation of the receive magnetic resonance imaging coil 114. FIG. 7 shows a cross-section view of the magnet 104. In this example the receive magnetic resonance imaging coil 114 again has multiple ambient light sensors 115. In the bore 106 of the magnet 104 there are again a number of lights for the magnet illumination system 107. The property of the light generated by the magnet illumination system 107 can vary as a function of angle about the axis of the magnet. The different ambient light sensors 115 therefore measure different light with different properties. This can be used to infer the orientation of the receive magnetic resonance imaging coil 114. As with the linear case illustrated in FIG. 6, the lights 107 can have their properties vary such as color, intensity, oscillation frequency, having modulation signal or other properties which enable the identification of the orientation of the receive magnetic resonance imaging coil 114.

The linear encoding illustrated in FIG. 6 and the radial encoding in FIG. 7 can be combined so that a very accurate picture of the position and orientation of the receive magnetic resonance imaging coil 114 can be determined. For example, there may be a modulation in one of these two coordinates and then a color or intensity may be used in another. The decision module 148 and/or the trained machine learning module 150 could be adapted for also determining the position and orientation using a scheme such as is illustrated in FIGS. 6 and 7. It should be noted that the example in FIG. 7 can also be modified where the ambient light sensors 115 are mounted on the wall of the bore of the magnet 106 and the light generating elements take their place on the receive magnetic resonance imaging coil 114. The various light generating elements can then produce light which is distinct and can be measured using the ambient light sensors 115.

State of the art Magnetic Resonance (MR) receive (RX) coil receivers (receive magnetic resonance imaging coil 114) are preferably calibrated in terms of time alignment (synchronization), gain and other parameters. This may provide a means to distinguish the position of the coil outside or inside scanner bore, independently from the actually existing measures. This helps to distinguish calibration failures due to a true defect from cases where the coil was just in the wrong position outside the bore.

For a part of these parameters a low power calibration signal is transmitted via the body coil. Unfortunately, when this calibration procedure fails, it is not clear if the coil (its preamp or the digitizer) is broken, or the coil is just outside the body coil where the calibration signal is too weak.

For radiation therapy or MR/PET it is beneficial to know the localization of the RF coil (mask) to prevent errors in therapy/treatment planning.

Currently, due to the uncertainty, not all failing calibration phases lead to a scan abort to avoid a too high false positive coil failure detection rate. That means that in certain cases with a true fault, scanning is performed, but results in image artefacts and the need for repetition of the scan.

To distinguish the two cases, one may determine the coil position inside (imaging position 200) or outside the body coil (loading position 121).

To create added value, the new measure may to be independent from the existing RF based components.

One measure is to equip each coil element with a photo diode (ambient light sensor 115) to detect ambient light 160, 162. When the light is coded in a different way outside and inside the scanner it is easy to determine the coil position.

Figure 8:
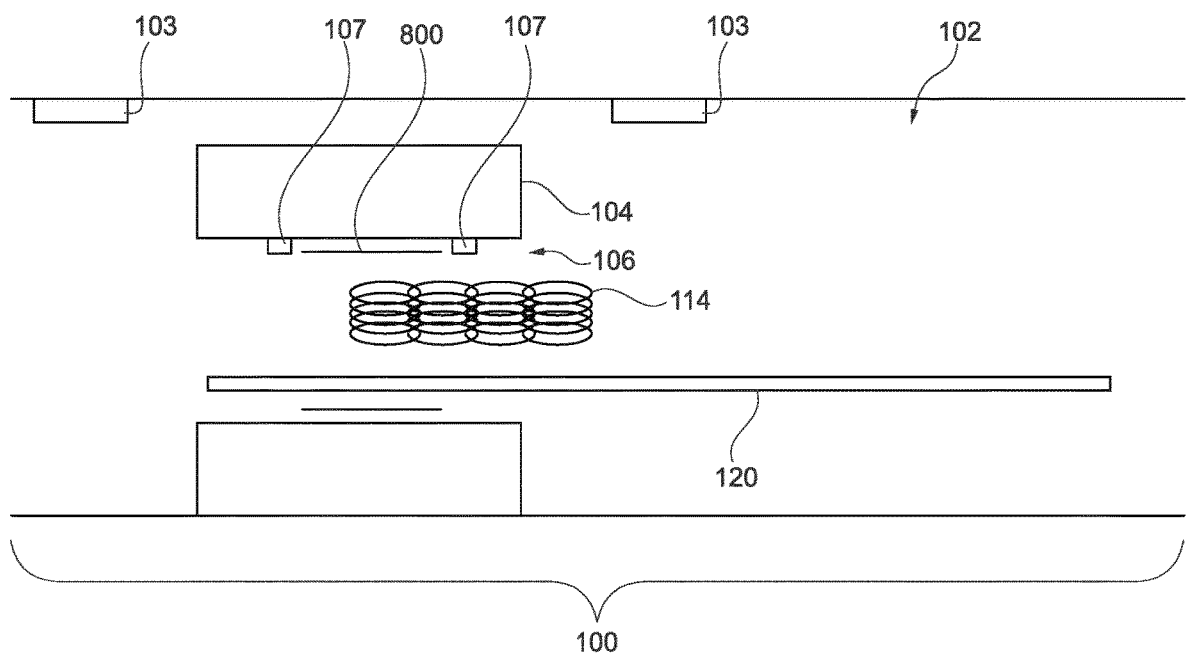
FIG. 8 illustrates a further example of a magnetic resonance imaging system.

FIG. 8 illustrates an alternative view of the magnetic resonance imaging system 100. The magnetic resonance imaging system is shown as additionally comprising a body coil 800. The body coil is not shown in FIGS. 1 and 2 but may also be installed there. The body coil 800 may be particularly useful when calibrating the receive magnetic resonance imaging coil 114. FIG. 8 above shows an over-view diagram. As usual the scanner is equipped with bore lights (magnet illumination system 107) and corresponding ceiling lamps (room illumination system 103) inside the cage.

Figure 9:
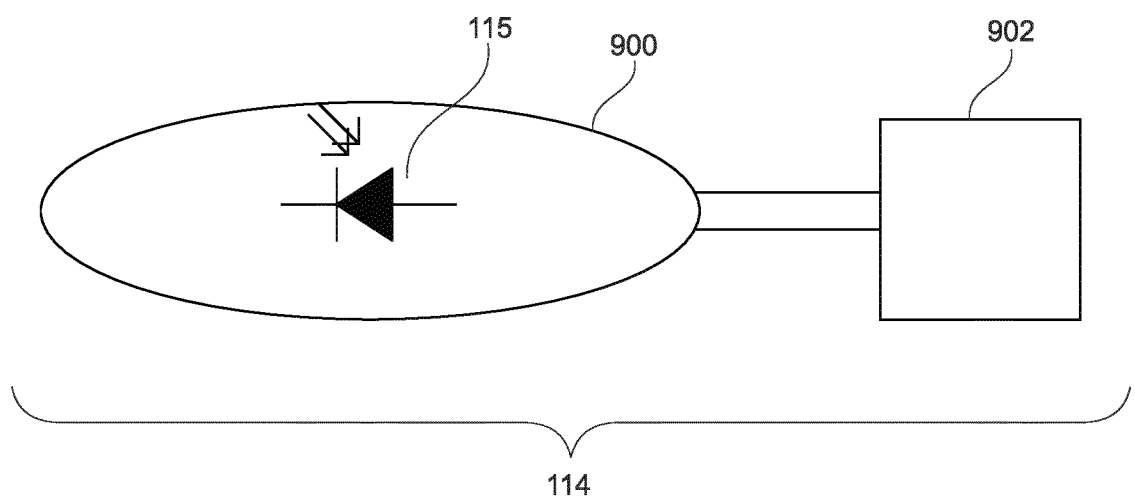
FIG. 9 illustrates an example of a receive magnetic resonance imaging coil.
Figure 10:
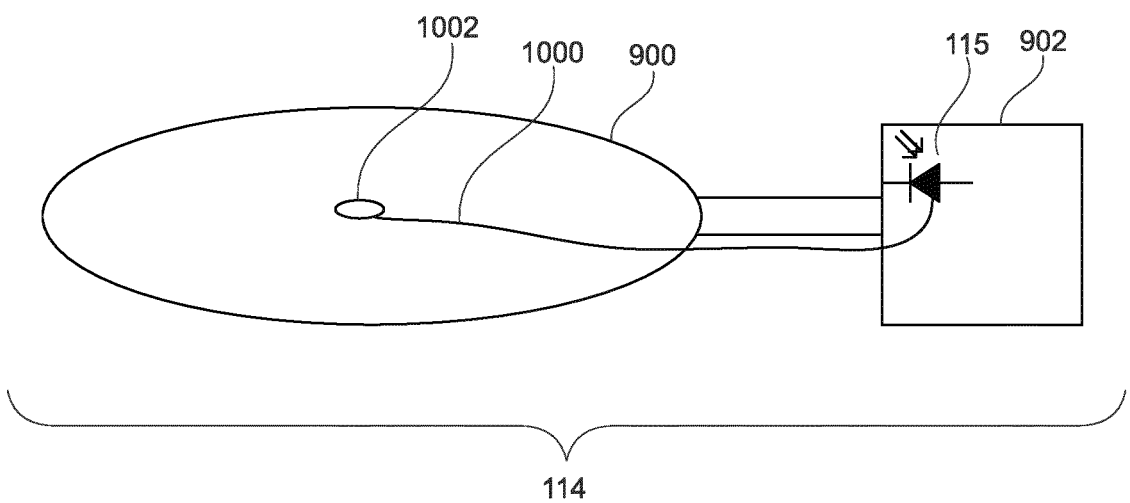
FIG. 10 illustrates an example of a receive magnetic resonance imaging coil.

In the given example, the coil array is actually placed in a way so that a part of it is inside the body coil (calibration works) and a part of it is outside (calibration prone to fail). FIGS. 9 and 10 below show a detailed sketch of one coil element 900. Each is equipped with at least a photo diode 115 detecting the ambient light. The diode can be placed at the center of the corresponding coil element 900, or when the coil is small enough it can be placed on the preamp or ADC PCB. Optionally, one could use a lens 1002 and an optical fiber 1000 to pick up light at a first position while the detector is placed at another position.

Usually the coil covers are made with translucent material so that the detector can be hidden underneath the coil covers. The AD conversion of the detector signal may be done as part of the digital coil infrastructure FIG. 9 illustrates an example of a receive magnetic resonance imaging coil 114. The receive magnetic resonance imaging coil comprises one or more coil elements 900 and a preamplifier 902. The ambient light sensor 115 is shown as being mounted within or about the coil elements 900. The ambient light sensor 115 would be mounted so that it is able to measure ambient light exposing on the surface of the receive magnetic resonance imaging coil 114.

FIG. 10 shows a further example of a receive magnetic resonance imaging coil. In this example the ambient light sensor 115 is attached or mounted to the preamplifier 902. This has the advantage of moving the electronics away from the coil elements 900. To get light to the ambient light sensor 115 a fiber optic 100 couples to a lens 1002 mounted on the surface of the receive magnetic resonance imaging coil 114. Only a single sensor 115 and fiber optic 1000 are shown but in this way a larger number of sensors 115 could be incorporated without disturbing the measurements made by the receive magnetic resonance imaging coil 114. This may for example allow more accurate determination of the position and orientation of the receive magnetic resonance imaging coil 114.

Actual coding of the light can be, for example only, done in the following way:
Different colors (warm white vs cold white)
Different intensity of light over time (e.g. 200 Hz oscillating ceiling light vs 100 Hz bore light, modulation not visible for the human eye)
Intensity of one component of light over time (RGB LEDs) When the coil moves into the bore it detects a change of the corresponding light property and reports it to the back end.

If the current lighting in ceiling and current bore lights produce distinct types of light, then it may be possible to implement examples without changing these lights or installing additional lights.

However, a standardization of the lighting simplifies the detection of the position, especially the detector technology and the definition of the thresholds.

In a further advancement the bore lights near the service end and those at the patient end emit differently coded light as well. This allows to localize the coil along the bore.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
102 examination room
103 room illumination system
104 main magnet
106 bore of magnet
107 magnet illumination system
108 imaging zone
110 magnetic field gradient coils
112 magnetic field gradient coil power supply
114 receive magnetic resonance imaging coil
115 ambient light sensor
116 transceiver
118 subject
120 subject support
121 loading position
122 actuator
126 computer system
128 hardware interface
130 processor
132 user interface
134 computer memory
140 machine executable instructions
142 pulse sequence commands
144 light data
146 signal
148 decision module
150 trained machine learning module
152 initial light data
154 optional calibration commands
160 first type of light
162 second type of light
200 imaging position
209 region of interest
240 calibration result
242 magnetic resonnace imaging data
244 magentic resonance image
300 magnetic resonance imaging system
302 light generating element
304 light from light generating element
500 move the subject support from the loading position to the imaging position
502 acquire the light data using the at least one ambient light data when the subject support is in the imaging position 504 determine if the receive magnetic resonance imaging coil is positioned for acquiring the magnetic resonance imaging data using the light data 506 provide a misaligned signal if the receive magnetic resonance imaging coil is not positioned for acquiring the magnetic resonance imaging data 800 body coil 900 coil elements 902 preamp 1000 optical fiber 1002 lens

The invention claimed is:

1. A magnetic resonance imaging system configured for acquiring magnetic resonance imaging data from an imaging zone, wherein the magnetic resonance imaging system comprises:
a main magnet configured for generating a B0 magnetic field within the imaging zone;
a subject support configured for moving a subject between a loading position and an imaging position;
a receive magnetic resonance imaging coil configured for being placed on the subject;
a light detection system comprising multiple ambient light sensors, wherein the light detection system is configured to measure spatially coded light data from ambient illumination, wherein the ambient illumination is spatially encoded in that it has a physical aspect that is different between the loading and imaging positions, wherein the light detection system is mounted to the receive magnetic resonance imaging coil, and wherein the multiple ambient light sensors are configured for measuring ambient light distributed across a surface of the receive magnetic resonance imaging coil;
a memory configured to store machine executable instructions;
a processor configured to control the magnetic resonance imaging system, wherein execution of the machine executable instructions causes the processor to:
control the subject support to move from the loading position to the imaging position;
acquire the spatially coded light data using the multiple ambient light sensors when the subject support is in the imaging position;
determine if the receive magnetic resonance imaging coil is positioned for acquiring the magnetic resonance imaging data using the spatially coded light data; and
provide a signal if the receive magnetic resonance imaging coil is positioned for acquiring the magnetic resonance imaging data.

2. The magnetic resonance imaging system of claim 1, wherein the magnetic resonance imaging system further includes a multi-channel radio-frequency system configured to acquire the magnetic resonance imaging data, wherein the radio-frequency system includes a body coil and the receive magnetic resonance imaging coil, wherein the receive magnetic resonance imaging coil comprises multiple receive elements and supports multiple channels, wherein the memory further contains calibration commands configured to control the magnetic resonance imaging system to perform a calibration of the multiple receive elements of the receive magnetic resonance imaging coil using the body coil, wherein execution of the machine executable instructions further causes the processor to:
calibrate the multiple channels of the receive magnetic resonance imaging coil by executing the calibration commands; and
provide a hardware failure signal if the calibration fails with the signal indicating that the receive magnetic resonance imaging coil is properly positioned.

3. The magnetic resonance imaging system of claim 1, wherein the magnetic resonance imaging system comprises an examination room for housing the main magnet, wherein the examination room comprises a room illumination system, wherein the main magnet comprises a magnet illumination system for illuminating the imaging zone, wherein the room illumination system is configured for producing a first type of light, wherein the magnet illumination system is configured to produce a second type of light, wherein execution of the machine executable instructions causes the processor to determine if the receive magnetic resonance imaging coil is positioned to acquire the magnetic resonance imaging data by differentiating between the first type of light and the second type of light.

4. The magnetic resonance imaging system of claim 3, wherein the first type of light differs from the second type of light by any one of the following: a color, an intensity, an oscillation frequency, an intensity of a color component, a modulation of the light, and combinations thereof.

5. The magnetic resonance imaging system of claim 3, wherein the magnet illumination system is configured to produce light with a spatially dependent frequency, a spatially dependent color encoding, and/or a spatially dependent modulation.

6. The magnetic resonance imaging system of claim 5, wherein execution of the machine executable instructions further causes the processor to determine a spatial position and/or orientation of the receive magnetic resonance imaging coil using the spatially dependent frequency, the spatially dependent color encoding, and/or the spatially dependent modulation produced by the magnet illumination system.

7. The magnetic resonance imaging system of claim 1, wherein the receive magnetic resonance imaging coil comprises a preamplifier, wherein the ambient light sensors are attached to the preamplifier, wherein the receive magnetic resonance imaging coil comprises an optical fiber for each of the ambient light sensors, wherein each optical fiber is configured to channel light from the surface of the receive magnetic resonance imaging coil to one of the ambient light sensors.

8. The magnetic resonance imaging system of claim 1, wherein execution of the machine executable instructions causes the processor to determine whether the receive magnetic resonance imaging coil is positioned to acquire the magnetic resonance imaging data by inputting the spatially coded light data into a decision module programmed to compare the spatially coded light data to a set of predetermined criteria.

9. The magnetic resonance imaging system of claim 1, wherein execution of the machine executable instructions causes the processor to determine if the receive magnetic resonance imaging coil is positioned to acquire the magnetic resonance imaging data by inputting the spatially coded light data into a trained machine learning module.

10. The magnetic resonance imaging system of claim 1, wherein the physical aspect of the ambient illumination comprises at least one of: a color of the ambient illumination, an intensity of the ambient illumination, an oscillation frequency of light of the ambient illumination, an intensity of a color component of the ambient illumination, and a modulation of light of the ambient illumination.

11. A tangible computer program product comprising machine executable instructions, wherein the machine executable instructions are configured for execution by a processor controlling a magnetic resonance imaging system, wherein the magnetic resonance imaging system is configured to acquire magnetic resonance imaging data from an imaging zone, wherein the magnetic resonance imaging system comprises a main magnet configured for generating a B0 magnetic field within the imaging zone; wherein the magnetic resonance imaging system further comprises a subject support configured for moving a subject between a loading position and an imaging position; wherein the magnetic resonance imaging system further comprises a receive magnetic resonance imaging coil configured to be placed on the subject, wherein the magnetic resonance imaging system further comprises a light detection system comprising multiple ambient light sensors, wherein the light detection system is configured to measure spatially coded light data from ambient illumination, wherein the ambient illumination is spatially encoded in that it has a physical aspect that is different between the loading and imaging positions, wherein the light detection system is mounted to the receive magnetic resonance imaging coil and wherein the multiple ambient light sensors are configured to measure ambient light distributed across a surface of the receive magnetic resonance imaging coil; wherein execution of the machine executable instructions causes the processor to:

control the subject support to move from the loading position to the imaging position;
acquire the spatially coded light data using the multiple ambient light sensors when the subject support is in the imaging position;
determine if the receive magnetic resonance imaging coil is positioned for acquiring the magnetic resonance imaging data using the spatially coded light data; and
provide a signal if the receive magnetic resonance imaging coil is positioned for acquiring the magnetic resonance imaging data.

12. A method of operating a magnetic resonance imaging system, wherein the method is configured to operate a magnetic resonance imaging system, wherein the magnetic resonance imaging system is configured for acquiring magnetic resonance imaging data from an imaging zone, wherein the magnetic resonance imaging system comprises a main magnet configured for generating a B0 magnetic field within the imaging zone, wherein the magnetic resonance imaging system further comprises a subject support configured for moving a subject between a loading position and an imaging position, wherein the magnetic resonance imaging system further comprises a receive magnetic resonance imaging coil configured for being placed on the subject, wherein the magnetic resonance imaging system further comprises a light detection system comprising multiple ambient light sensors, wherein the light detection system is configured to measure spatially coded light data from ambient illumination, wherein the ambient illumination is spatially encoded in that it has a physical aspect that is different between the loading and imaging positions, wherein the light detection system is mounted to the receive magnetic resonance imaging coil and wherein the multiple ambient light sensors are configured for measuring ambient light distributed across a surface of the receive magnetic resonance imaging coil, wherein the method comprises:

moving the subject support from the loading position to the imaging position;
acquiring the spatially coded light data using the multiple ambient light sensors when the subject support is in the imaging position;
determining if the receive magnetic resonance imaging coil is positioned for acquiring the magnetic resonance imaging data using the spatially coded light data; and
providing a signal if the receive magnetic resonance imaging coil is positioned for acquiring the magnetic resonance imaging data.

13. The method of claim 12, wherein the magnetic resonance imaging system further includes a multi-channel radio-frequency system configured to acquire the magnetic resonance imaging data, wherein the radio-frequency system includes a body coil and the receive magnetic resonance imaging coil, wherein the receive magnetic resonance imaging coil comprises multiple receive elements and supports multiple channels, wherein the memory further contains calibration commands configured to control the magnetic resonance imaging system to perform a calibration of the multiple receive elements of the receive magnetic resonance imaging coil using the body coil, wherein the method further comprises:

calibrating the multiple channels of the receive magnetic resonance imaging coil by executing the calibration commands; and
providing a hardware failure signal if the calibration fails with the signal indicating that the receive magnetic resonance imaging coil is properly positioned.

14. The method of claim 12, wherein the magnetic resonance imaging system comprises an examination room for housing the main magnet, wherein the examination room comprises a room illumination system, wherein the main magnet comprises a magnet illumination system for illuminating the imaging zone, wherein the room illumination system is configured for producing a first type of light, wherein the magnet illumination system is configured to produce a second type of light, wherein the method further comprises:

determining if the receive magnetic resonance imaging coil is positioned to acquire the magnetic resonance imaging data by differentiating between the first type of light and the second type of light.

15. The method of claim 14, wherein the first type of light differs from the second type of light by any one of the following: a color, an intensity, an oscillation frequency, an intensity of a color component, a modulation of the light, and combinations thereof.

16. The method of claim 14, wherein the magnet illumination system is configured to produce light with a spatially dependent frequency, a spatially dependent color encoding, and/or a spatially dependent modulation, wherein the method further comprises:

determining a spatial position and/or orientation of the receive magnetic resonance imaging coil using the spatially dependent frequency, the spatially dependent color encoding, and/or the spatially dependent modulation produced by the magnet illumination system.

17. The method of claim 12, wherein the receive magnetic resonance imaging coil comprises a preamplifier, wherein the ambient light sensors are attached to the preamplifier, wherein the receive magnetic resonance imaging coil comprises an optical fiber for each of the ambient light sensors, wherein the method further comprises:

channeling light from the surface of the receive magnetic resonance imaging coil to one of the ambient light sensors.

18. The method of claim 12, further comprising:
determining whether the receive magnetic resonance imaging coil is positioned to acquire the magnetic resonance imaging data by inputting the spatially coded light data into a decision module programmed to compare the spatially coded light data to a set of predetermined criteria.

19. The method of claim 12, further comprising:
determining whether the receive magnetic resonance imaging coil is positioned to acquire the magnetic resonance imaging data by inputting the spatially coded light data into a trained machine learning module.

20. The method of claim 12, wherein the physical aspect of the ambient illumination comprises at least one of: a color of the ambient illumination, an intensity of the ambient illumination, an oscillation frequency of light of the ambient illumination, an intensity of a color component of the ambient illumination, and a modulation of light of the ambient illumination.

* * * * *